United States Patent [19]

Davenport

[11] Patent Number: 5,322,794
[45] Date of Patent: Jun. 21, 1994

[54] FLUORESCENT PHOSPHOLIPID ANALOGS AND FATTY ACID DERIVATIVES

[76] Inventor: Lesley Davenport, Dept. Chemistry, Brooklyn College of CUNY Bedford Ave. & Ave. H, Brooklyn, N.Y. 11210

[21] Appl. No.: 18,210

[22] Filed: Feb. 16, 1993

[51] Int. Cl.$^5$ .................. G01N 33/92; G01N 21/76; C07C 69/76; C07C 69/95
[52] U.S. Cl. ................................. 436/71; 436/55; 436/56; 436/128; 436/172; 560/52; 560/53; 560/54; 560/101
[58] Field of Search ............... 560/52, 53, 54, 101; 436/55, 56, 71, 172, 800, 128

[56] References Cited

U.S. PATENT DOCUMENTS

| | | | |
|---|---|---|---|
| 4,978,625 | 12/1990 | Wagner et al. | 436/518 |
| 5,094,819 | 3/1992 | Yager et al. | 422/82.07 |
| 5,094,959 | 3/1992 | Allen et al. | 436/172 |

OTHER PUBLICATIONS

Vincent, et al., "Nanosecond Fluorescence Anisotropy Decays of n-(9-Anthroyloxy) Fatty Acids in Dipalmitolyphosphatidylcholine vesicles with Regard to Isotropic Solvents." Biochemistry 21, 708–716 (1982).
Brockerhoff, H. "Determination of the Positional Distribution of Fatty Acids in Glycerolipids." in Methods in Enzymology 35, 315–325 (1975).
Morgan et al., "The Use of a Phospholipid Analogue of Diphenly 1,3,5-Hexatriene to study Mellitin-induced Fusion of Small Unilamellar Phospholipid Vesicles." Biochemica et Biophys Acta 692, 196–201 (1982).
Han et al., "Nanosecond Time-Resolved Flourescence Kinetic Studies of the 5,5'-Dithiobis (2-nitrobenzoic acid) Reaction with Enzyme 1 of the Phosphoenolpyruvate:Glucose Phosphotransferase System," Analytical Biochemistry 161, 479–486 (1987).
Clar et al., "1:2-Benzocoronene and Napth(2":3"-1:2-)coronene." Journal of the Chemical Society, 2:1577–1579 (1958).
Slepushkin et al., "Interation of Influenza Virus with Gangliosides and Liposomes Containing Gangliosides," European Journal of Biochemistry 173, 599–605 (1988).
Molotkovsky et al., "Synthesis and characterization of new fluorescent glycolipis probes. Molecular Organisation of glycosphingolipids in mixed-composition lipid bilayers." Chem. Phys. Lipids 58, 199–212 (1991).
Gromova et al., "Anthrylvinyl-labeled phospholipids as fluorescent membrane probes. The action of melittin on multilipid systems." Chem. Phys. Lipids 60, 235–246 (1992).
Lianos et al., "Complex Formation Between Alcohols and the Aromatic Hydrocarbons Pyrene and 1-Methylpyrene" Photochem. Photobiol. 29, 843–846 (1979).
Han et al., "Enhancement of Time-Resolved Fluorescence Spectroscopy by Overdetermination," in Fluorescent Biomolecules, Jameson D. M. et al. Eds., Plenum Press, pp. 33–59 (1989).
Radda, G. K. "Fluorescent Probes in Membrane Studies" in Methods in Membrane Biology, Kam, E. D. Ed., vol. IV, Plenum Press., pp. 97–188.

Primary Examiner—Nina Bhat

[57] ABSTRACT

Fluorescence probes are described comprising coronene fluorophores chemically attached to lipids or membrane-mimetic molecules via hydrocarbon spacers of defined length. Also described is a method for determining lipid packing and dynamics in membranes, a method for estimating hydrodynamic properties of macromolecules and macromolecular complexes, and a method for measuring changes in $Ca^{+2}$ concentrations in or near membranes.

11 Claims, 1 Drawing Sheet

FLUORESCENT PHOSPHOLIPID ANALOGS AND FATTY ACID DERIVATIVES

This work was supported in part by a grants from the National Science Foundation and the American Heart Association (New York City Affiliate), who may have rights in this invention.

FIELD OF THE INVENTION

The present invention relates to fluorescence probes comprising coronene derivative fluorophores chemically attached to either long-chain fatty acids, or to lipids via hydrocarbon spacers of defined length.

BACKGROUND OF THE INVENTION

Lipid soluble molecules bound to planar fluorescent dyes are useful as molecular reporters of their local environment (see Vincent et al., Biochem. Biophys. Res. Comm. 107, 914 (1982); Vincent et al., Biochemistry 21, 708 (1982); Slepushkin et al., Eur. J. Biochem. 173, 599 (1988); Molotkovsky et al., Chem. Phys. Lipids 58, 199 (1991); Gromova et al. Chem. Phys. Lipids 60, 235 (1992)). After introduction of these molecules into surfactant-containing matrices including but not limited to phospholipid bilayers, planar bilayers, or bulk solutions, polarized fluorescence spectroscopy may be employed to estimate the rotational motions or the fluorescent moiety, which in turn reflects the physical state of the organization of the matrix surrounding the fluorescent dye A major limitation of the usefulness of these fluorescent probes is their relatively short fluorescence lifetime. As a result, the interpretation of the dye rotational motions are complex due to detection of both in-plane and out-of-plane rotational motions (see Vincent et al., BBRC 107; 914 (1982); Vincent et al., Biochemistry 21; 708 (1982)). The probes comprising the present invention overcome this disadvantage. Due to their long fluorescent lifetimes, the rapid in-plane motions of the coronene probes are virtually not detected. This results in simplified interpretation of the polarized fluorescence data, and allows detection of events occurring on the submicrosecond timescale, which were previously undetectable using polarized fluorescence spectroscopy. Until the present invention, dynamics on the submicrosecond timescale have not been extensively investigated because of the lack of a suitable probe.

The rates of rotation on this extended timescale, previously undetectable by the use of polarized fluorescence spectroscopy, reflect important information about the local environment surrounding the molecular probe which is not obtainable by presently available fluorescence probes. The probes of the invention widen the window of investigation possible to allow study of these longer-lived phenomena, which include rotation rates of large proteins and molecular complexes from which hydrodynamic properties including shape and axial ratios can be estimated.

SUMMARY OF THE INVENTION

Figure 1:
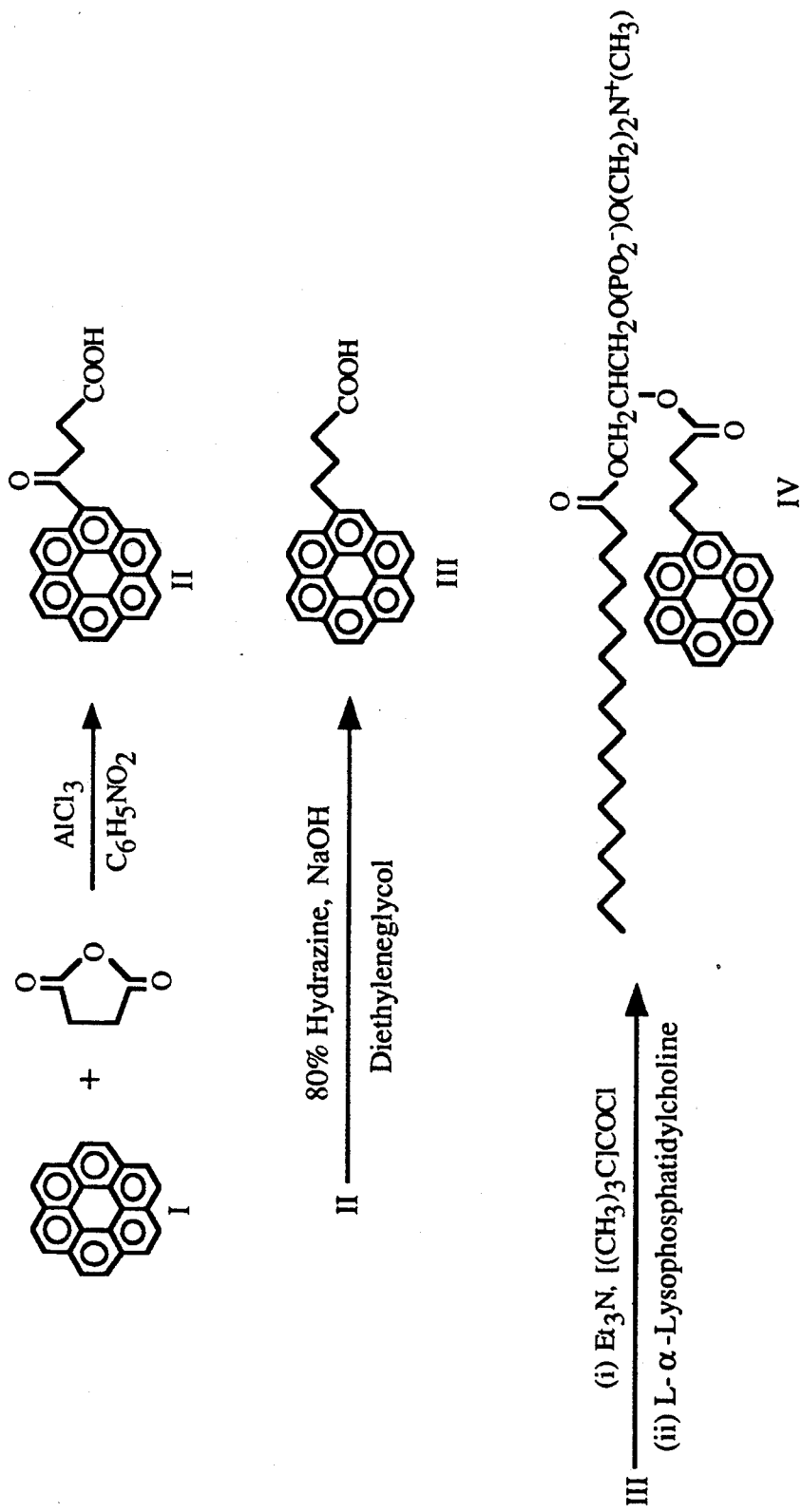
FIG. 1 summarizes the synthetic route from coronene to 4-coronenyl butyric phosphatidylcholine (Cor-PC), which is described in detail in the Examples.

An object of the present invention is to provide fluorescent probes of formula I:

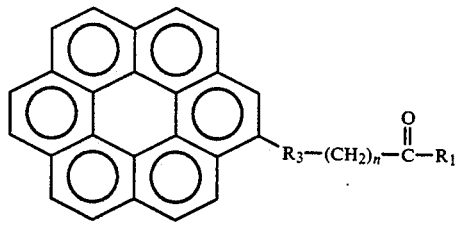

in which $R_1$ is a lipid radical or a membrane mimetic radical, $R_3$ is methylene or carbonyl, and n indicates the number of methylene groups between $R_3$ and the carbonyl group, which may be from 1 to 25.

Another object of the present invention is to provide fluorescent probes of formula II:

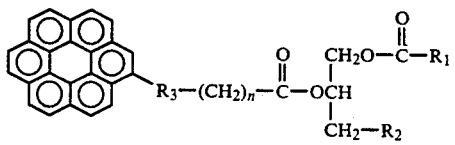

in which the coronene fluorophore is bound to $R_3$, which may be methylene or carbonyl, which is bound through a straight-chain alkyl spacer of n methylene groups to a carbonyl group, which is in turn bound to the oxygen of the center carbon of a substituted glycerol. The oxygen of the $C_1$ carbon of the glycerol moiety participates in an ester linkage with a carboxylic acid or fatty acid (i.e., a straight chain carboxylic acid longer than four carbon atom in length). The particular carboxylic acid or fatty acid is determined by selection of radical $R_1$, which is a straight chain hydrocarbon group which may contain one or more double or triple bonds, and which may be up to 25 carbon atoms in length. The $C_3$ carbon of the glycerol moiety is bound either to a phosphate group or a substituted phosphate group selected from phosphocholine, phosphoinositol, phosphoserine, phosphoethanolamine, phosphoglycerol, or substituted phosphoglycerol. The $C_3$ carbon may also be bound to an oxygen atom which is bound to a carbonyl group which is in turn bound to a straight chain hydrocarbon group which may contain one or more double or triple bonds, and which may be up to 25 carbon atoms in length.

A further object of the present invention is to provide fluorescent probes of formula III:

![formula III structure with coronene, $R_3-(CH_2)_n-C-OCH_2$, $HC-O-C-R_1$, $CH_2-R_2$]

in which the coronene fluorophore is bound to $R_3$, which may be methylene or carbonyl, which is bound through a straight-chain alkyl spacer of n methylene groups to a carbonyl group, which is in turn bound to the oxygen of the $C_1$ carbon of a substituted glycerol. The oxygen of the $C_2$ carbon of the glycerol moiety participates in an ester linkage with a carboxylic acid or fatty acid (i.e., a straight chain carboxylic acid longer than four carbon atom in length). The particular carboxylic acid or fatty acid is determined by selection of radical $R_1$, which is a straight chain hydrocarbon group which may contain one or more double or triple bonds, and which may be up to 25 carbon atoms in length. The $C_3$ carbon of the glycerol moiety is bound either to a phosphate group or a substituted phosphate group selected from phosphocholine, phosphoinositol, phosphoserine, phosphoethanolamine, phosphoglycerol, or substituted phosphoglycerol. The $C_3$ carbon may also be bound to an oxygen atom which is bound to a carbonyl group which is in turn bound to a straight chain hydrocarbon group which may contain one or more double or triple bonds, and which may be up to 25 carbon atoms in length.

The present invention provides a method of determining the lipid packing and lipid dynamics in a membrane comprising introducing a probe of the present invention into a membrane by cosonication, coextrusion, or addition as a micelle or vesicle carrier, measuring the rotational motion of the probe using steady state or time-resolved polarized fluorescence spectroscopy, and thereby determining the lipid packing and lipid dynamics.

The present invention also provides a method of estimating hydrodynamic properties of macromolecules or macromolecular complexes comprising chemically binding the probes of the present invention to a macromolecule or macromolecular complex, and measuring the rotational motion of the probe using steady state or time-resolved polarized fluorescence spectroscopy.

The present invention also provides a method of measuring changes in a $Ca^{+2}$ concentration in or near a membrane comprising introducing a probe of the present invention into a membrane by cosonication, coextrusion, or addition as a micelle, introducing phospholipase $A_2$ into or near the membrane, and measuring the rotational motion of the released coronene probes using steady state or time-resolved polarized fluorescence spectroscopy and/or microscopy.

DETAILED DESCRIPTION OF THE INVENTION

The present invention provides probes having coronene as the fluorophore, which have unusually long fluorescence lifetimes. For these probes the observed rotational motions are simplified, because the unusually long fluorescence lifetime of the coronene group, combined with its planar symmetry, allows determination of out-of-plane submicrosecond rotational motions of the dye. These molecules therefore represent a new class of fluorescence probes which report submicrosecond dynamics.

The present invention comprises fluorescent probes of formula I:

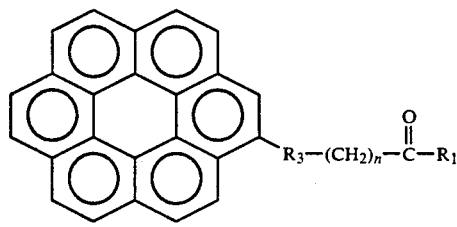

wherein $R_1$ is a lipid radical or a membrane mimetic radical, $R_3$ is methylene or carbonyl, and n indicates the number of methylene groups between $R_3$ and the carbonyl group, which may be from to 25. Membrane mimetic compounds are those which form membranes in solution, or which aggregate in solution to form macromolecular structures the properties of which mimic those of membranes. The distance between the coronene fluorophore and the lipid or membrane-mimetic radical is determined by n, which may be from 1 to 25.

In one embodiment of the invention, $R_1$ may be selected from sphingolipids, glycerolipids, diacylglycerols, ceramides, glycolipids, glycosphingolipids and cardiolipin.

In another embodiment of the invention, $R_1$ may be a phospholipid radical.

In another embodiment of the invention, $R_1$ may be a monoacylglycerol phosphate radical, a diacylglycerolphosphate radical, or a sphingomyelin radical.

In another embodiment of the invention, $R_1$ is hydroxyl.

In another embodiment of the invention, $R_1$ is a cholesterol radical.

The present invention also comprises fluorescent probes of formula II:

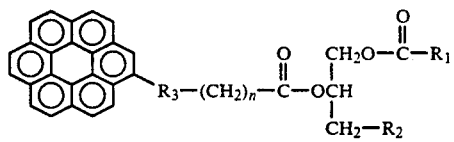

wherein the coronene fluorophore is bound to $R_3$, which may be methylene or carbonyl, which is bound through a straight-chain alkyl spacer of n methylene groups to a carbonyl group, which is in turn bound to the oxygen of the center carbon of a substituted glycerol. The oxygen of the $C_1$ carbon of the glycerol moiety participates in an ester linkage with a carboxylic acid or fatty acid (i.e., a straight chain carboxylic acid longer than four carbon atom in length). The particular carboxylic acid or fatty acid is determined by selection of radical $R_1$, which is a straight chain hydrocarbon group which may contain one or more double or triple bonds, and which may be up to 25 carbon atoms in length. The $C_3$ carbon of the glycerol moiety is bound either to a phosphate group or a substituted phosphate group selected from phosphocholine, phosphoinositol, phosphoserine, phosphoethanolamine, phosphoglycerol, or substituted phosphoglycerol. The $C_3$ carbon may also be bound to an oxygen atom which is bound to a carbonyl group which is in turn bound to a straight chain hydrocarbon group which may contain one or more double or triple bonds, and which may be up to 25 carbon atoms in length.

The present invention also comprises fluorescent probes of formula III:

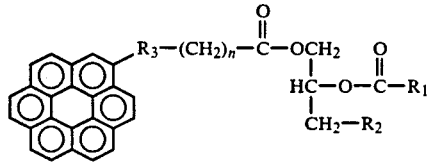

wherein the coronene fluorophore is bound to $R_3$, which may be methylene or carbonyl, which is bound through a straight-chain alkyl spacer of n methylene groups to a carbonyl group, which is in turn bound to the oxygen of the $C_1$ carbon of a substituted glycerol. The oxygen of the $C_2$ carbon of the glycerol moiety participates in an ester linkage with a carboxylic acid or fatty acid (i.e., a straight chain carboxylic acid longer than four carbon atom in length). The particular carboxylic acid or fatty acid is determined by selection of radical $R_1$, which is a straight chain hydrocarbon group which may contain one or more double or triple bonds, and which may be up to 25 carbon atoms in length. The $C_3$ carbon of the glycerol moiety is bound either to a phosphate group or a substituted phosphate group selected from phosphocholine, phosphoinositol, phosphoserine, phosphoethanolamine, phosphoglycerol, or substituted phosphoglycerol. The $C_3$ carbon may also be bound to an oxygen atom which is bound to a carbonyl group which is in turn bound to a straight chain hydrocarbon group which may contain one or more double or triple bonds, and which may be up to 25 carbon atoms in length.

The present invention also comprises a method of determining the lipid packing and lipid dynamics in a membrane comprising introducing a probe of the present invention into a membrane by cosonication, coextrusion, or addition as a micelle or vesicle carrier, measuring the rotational motion of the probe using steady state or time-resolved polarized fluorescence spectroscopy, and thereby determining the lipid packing and lipid dynamics.

Lipid pacing and dynamics are determined by techniques standard in the art. After the sample of interest is doped with a probe of the invention at low (typically nanomolar) concentration, polarized fluorescence data is then collected by either steady-state excitation or time-resolved techniques. It is understood by those skilled in the art that for both methods, the polarized fluorescence emissions from the solution are analyzed as either the vertical $I_v$ or horizontal $I_H$ orientation, using a polarizer oriented in the emission path.

Polarized steady state emissions of the probes of the invention may be interpreted using methods which are known in the art and the subject of extensive review. See for example 'Principles of Fluorescence Spectroscopy' J. R. Lakowicz (1983) Plenum Press, N.Y. (chapter 5; pages 112–153). It is known that to determine lipid dynamics and packing from steady-state measurements, the experimentally collected polarized fluorescence data may be used to calculate a value of the average steady-state emission anisotropy ($<r>$), which is a measure of rotational motion of the fluorescence probe molecule. $<r>$ is determined from the equation:

$$<r> = (G \cdot I_{VV} - I_{VH})/(G \cdot I_{VV} + 2I_{VH}) \text{ and}$$
$$G = (I_{HH}/I_{HV})$$

wherein G is an instrumental correction factor and the first subscript refers to the orientation of the excitation polarizer, and the second to that of the emission polarizer.

Practitioners in the art will recognize that the value of $<r>$ reflects the hinderance imposed by the lipid (i.e. packing constraints) on the rotations of the fluorescent probe. To determine $r_o$, the limiting maximum value for $<r>$, the probe of the invention is placed in a frozen crystal, and $<r>$ is measured. Systems having dense lipid packing will therefore have measured values of $<r>$ which approach $r_0$. Similarly, systems with relatively loose lipid packing exhibit lower values of $<r>$. It is known that if a fluorescence probe is placed in an isotropic solvent such as ethanol, (e.g., one which allows complete freedom of probe rotation) the value of '$r$>' is zero. See 'Principles of Fluorescence Spectroscopy' J. R. Lakowicz (1983) Plenum Press, N.Y. (chapter 5; pages 112–153).

The measurement of $<r>$ for probes of the invention may be used to provide information of the "microviscosity" (" ") of the lipid environment. These values are particularly useful in the study of clinically relevant membrane disorders (see for example 'Principles of Fluorescence Spectroscopy' J. R. Lakowicz (1983) Plenum Press, N.Y. (chapter 5; pages 139–142); M. Shinitzky & Y Barenholz (1974) Journal of Biological Chemistry, Volume 249, Pages 2652-2657), and are determined by use of the well-known Perrin equation:

$$r_0/<r> = 1 + C(r)((\tau)/\eta)$$

where $<r>$ and $r_o$ are the measured and limiting fluorescence anisotropies, T is the absolute temperature, $\tau$ is the excited-state lifetime and $\eta$ is the viscosity of the medium. C(r) is a parameter which relates to the molecular shape of the fluorophore and has a specific value for each '$r$>'. It is known in the art to employ calibration curves of $r_0/<r>$ versus $T(\tau/\eta)$ for a solvent of known viscosity, for subsequent evaluation of the membrane "microviscosity ( )" from measured $<r>$ values, where T and $\tau$ are measured for the probe of interest. See 'Principles of Fluorescence Spectroscopy' J. R. Lakowicz (1983) Plenum Press, N.Y., (chapter 5; pages 134–142); M. Shinitzky & Y. Barenholz (1974) Journal of Biological Chemistry, Volume 249, Pages 2652–2657).

It will be appreciated that it is possible to determine lipid dynamics and packing from time-resolved measurements the probes of the invention. Unlike steady-state excitation, the time-dependent measurement resolves complex motions, such as rotation as asymmetric or flexible molecules in solution and can be applied to the determination of the dynamic structure of biomembranes. See for example 'Principles of Fluorescence Spectroscopy' J. R. Lakowicz (1983) Plenum Press, N.Y. (chapter 6; pages 155–185); K, Kinosita, Jr., S. Kawato & A. Kiegami (1977) Biophysical Journal, Volume 20, pages 289–305. Several models have been employed by those in the art to interpret the polarized fluorescence data. For example, heterogenous vs. homogeneous distribution of the "probe" in the bilayer matrix. These are well-known to those in the art and extensively documented in the literature. See for example 'Principles of Fluorescence Spectroscopy' J. R. Lakowicz (1983) Plenum Press, N.Y. (chapter 6; pages 155–185); L. Davenport J. R. Knutson & L. Brand (1989) 'Subcellular Biochemistry', (chapter 4, pages 145–188). In either case, the data is analyzed b applying to the exponential polarized fluorescence decay (r(t)) profiles an iterative non-linear least squares fitting program. The fitting equation used in biomembrane systems generally includes a residual ($r_\infty$) or persistent anisotropy term:
where:

$$r(t) = (r_0 - r_\infty)\Sigma_j e^{-t/\phi_j} + r_\infty$$

In all models used for determination of the dynamics and packing of lipids by fluorescence techniques, it is understood by those in the art that the value of the rotational correlation time ($\phi$, in nanoseconds) provides information on the dynamics of lipid motions, whereas the $r_\infty$ term represents the degree of anisotropy of the equilibrium orientation of the probe. It will be appreciated that the $r_\infty$ term can be related to the so-called "order parameter" ("S"), also commonly measured rom magnetic resonance methods ($S^2=(r_0/r_\infty)$), which provides information on the lipid ordering or packing within the biomembrane matrix. All models share the common feature that the rotational motion of the probe molecule is determined and that rotational motion reflects the dynamic nature of the lipid environment.

The present invention also comprises a method of estimating hydrodynamic properties of macromolecules or macromolecular complexes comprising chemically binding the probes of the present invention to a macromolecule or macromolecular complex, and measuring the rotational motion of the probe using steady state or time-resolved polarized fluorescence spectroscopy.

For example, to determine the size of a protein, a probe of the invention is covalently bound to the protein or macromolecule of interest, through a maleimide or other such functional group. The functional groupings used for such tagging, and the methods for such tagging are both well known in the art. Polarized fluorescence measurements are then made, and the anisotropy ($<r>$) measured. Insertion of $<r>$ into the well-known Perrin equation yields the volume of the hydrated molecule V. Those skilled in the art will recognize that for these purposes, the Perrin equation takes the form:

$$r_0/<r> = 1+(kT\tau)/(\eta V)$$

where:
k=Boltzman's constant
T=absolute temperature
$\eta$=solvent viscosity
V=volume of hydrated molecule
r=observed anisotropy
$r_0$=is the limiting $<r>$ value
$\tau$=the measured fluorescence lifetime Those skilled in the art will also appreciate that from V, the molecular weight of the macromolecule (M) may be is made via the equation:

$$\phi = \eta V/kT \leq \eta M/kT(v+h)$$

where $v$ is the specific volume of the protein and h is the hydration, typically 0.2 g water per gram of protein.

The present invention also comprises a method of measuring a changes in $Ca^{+2}$ concentration in or near a membrane comprising introducing a probe of the present invention into a membrane by cosonication, coextrusion, or addition as a micelle, introducing phospholipase $A_2$ into or near the membrane, and measuring the rotational motion of the released coronene probe using steady state or time-resolved polarized fluorescence spectroscopy and/or microscopy.

For example, after the phospholipase $A_2$ has been incorporated, an increase in $Ca^{+2}$ concentration will activate the phospholipase $A_2$, catalyzing the release of the coronene carboxylic acid moiety from the probe of the invention. A concomitant decrease int he value of $<r>$ measured by steady state methods would then be observed, as the coronene moiety of the probe now has less restricted motion.

In accordance with the present invention, coronene conjugated fluorescent probes may be synthesized by first reacting coronene with a dicarboxylic acid anhydride according to the procedure of Clar and Zanders (Journal of the Chemical Society 2, (1958) 1577–1579) to yield a coronenoyl carboxylic acid (probes of formula I, where $R_3$ is carbonyl). This compound may be reduced essentially as described by Clar and Zanders, with modifications to increase the yield of coronenyl carboxylic acid probe (probes of formula I, where $R_3$ is methylene). The Clar and Zanders procedures are known in the art.

The coronenyl and coronenoyl carboxylic acid probes may then be chemically bound to large macromolecules including but not limited to proteins, polymolecular complexes such as multienzyme complexes, protein-nucleic acid complexes and the like. The binding may be accomplished either specifically or nonspecifically, via their free carboxyl groups or facile modifications thereof, by techniques known in the art. The distance of the coronene fluorophore from the macromolecule of interest may be controlled by choice of the hydrocarbon spacer of the probe.

The coronenyl or coronenoyl carboxylic acid may be condensed with a lyso-lipid to yield a coronene-phospholipid conjugate fluorescent probe having a hydrocarbon spacer of defined length between the lipid head group and the coronene fluorophore or carbonyl coronene fluorophore (probes of formula II or III). Techniques for the condensation are known in the art, see for example the procedure of Morgan et al., Biochim et Biophys Acta, 692; 196 (1982).

In a preferred embodiment of the invention, the coronenephospholipid conjugate probe may be incorporated into phospholipid bilayers by technique of Morgan, et al., above, which is known in the art. Measurement of the rotational motions of the coronene fluorophore is accomplished by polarized fluorescence techniques known in the art (see the foregoing references, and Fluorescence Spectroscopy by J. R. Lakowicz; Plenum Press, New York).

All the probes of the present invention possess the planar coronene dye group, conferring upon the probes unique properties which enable the study of structural dynamics of a variety of proteins and lipid systems. Specifically. it is the unusually long fluorescence lifetime of the coronene group combined with the planar symmetry which by using polarized fluorescence spectroscopy, allows determination of out-of-plane submicrosecond rotational motions of the dye. These rates of rotation reflect important information about the local environment surrounding the molecular probe occurring on this extended timescale. The compounds of the present invention provide such information when incorporated into several types of lipid systems, including but not limited to lipid bilayers, single- or multi-lamellar lipid systems, micellar systems, and the like. Furthermore, variations in the spacer moiety of the probe allows detection at fixed defined locations across the bilayer width. The probes are also uniquely suited for the study of proteins, as the long fluorescence lifetime of coronene enables detection of rotational rates of large molecular weight proteins from which hydrodynamic properties including shape and axial ratios can be estimated.

The probes of the present invention afford additional advantages over probes presently available. The long fluorescence lifetimes of the coronene molecules are sensitive to polarity and oxygen tension in their local environment. These parameters vary markedly with the nature of the surrounding environment. For example, the fluorescence lifetime of coronene in isotropic solvent is significantly quenched due to oxygen saturation, however in the bilayer environment, where the viscosity restricts oxygen diffusion, the fluorescence lifetime is extremely long (~200ns). Hence the fluorescence lifetime of these probes are sensitive to organization or packing of their host matrix.

With deaeration of samples, the coronene probes have the additional advantage in that they phosphoresce. This deactivation route can provide an alternate, longer (microsecond) timescale for exploration of important biological phenomena.

Additionally, the coronene group can be readily excited using common laser excitation at 305nm using a frequency-doubled argon-ion laser. Many fluorescent membrane probes presently in use can only be excited in the 340–400nm range, which few commercially available lasers can easily achieve. The probes comprising the present invention are therefore more useful to researchers than other probes.

The probes of the present invention have potential diagnostic applications. Basic studies of lipid packing and dynamics in cell membranes on the submicrosecond timescale may provide the key to understanding important membrane mediated events e.g. passive Na+ 'leakage' through membrane defect sites, which can play a significant role in understanding and preventing the hypertensive condition.

In addition, the coronene-carboxylic acid moieties of the probes can be released from their parent phospholipids using the enzyme phospholipase $A_2$, by techniques known in the art (see Morgan et al., above). Phospholipase $A_2$ is activated by the presence of the biologically important cation $Ca^{2+}$, which has received a great deal of attention within the framework of membrane mediated signalling. Rotational properties of the dye attached to phospholipid and attached to the carboxylic acid will be different and can be detected using polarized fluorescence spectroscopy by techniques known in the art (see for example Lackowicz, above). The probes may therefore be employed to detect changes in $Ca^{+2}$ concentrations.

The following examples are given to illustrate the invention. It should be understood, however, that the invention is not to be limited to the specific conditions or details set forth in these examples.

EXAMPLES

Synthesis of 3-coronenoyl propionic acid

A Friedel-Crafts acylation of coronene was performed using the procedure of Clar and Zanders J. Chem. Soc. 2, (1958) 1577–1579, with the Coronene (100mg; FIG. 1, compound I) and succinic anhydride (73.4mg) were placed in a 10ml round-bottomed flask. Aluminum chloride (400mg) was dissolved in 3ml of nitrobenzene and injected slowly into the round-bottomed flask. The flask was then flushed with nitrogen and sealed. The mixture was stirred for four hours and cold 2M HCl (8ml) was added and the solution boiled for 10 minutes. A greenish-yellow precipitate was obtained. The crystals were filtered, washed with benzene, methanol and 2M HCl, and dried overnight under vacuum. The product (108mg; 82% yield) was recrystallized from xylene and judged pure using TLC analyses (Rf=0.53), using 50% ethanol/50% THF (v/v) as the developing solvent with silica gel G (40 micron) as the support medium. The keto-acid (FIG. 1, compound II) had a melting point of 243° C. IR and NMR analysis gave spectra consistent with the structure of the molecule, and in xylene had an absorption band at 444 nm, with $\epsilon_{340}$ in THF=24,914±80$M^{-1}cm^{-1}$.

Synthesis of 4-coronenyl butyric acid

The Huang-Minlon method was used essentially as described in Clar and Zanders (1958), with modifications to increase the overall yield of the acid: 3-coronenoyl propionic acid (100mg), 80% hydrated hydrazine (74.8 μl), NaOH (60mg), and diethylene glycol (249μl) were combined in a 5ml round-bottomed flask. The mixture was refluxed for 90 minutes at 180° C, then water and excess hydrazine hydrate were distilled off until the temperature rose to 200° C. The mixture was refluxed for an additional 3.5 hours at 195° C., cooled to room temperature and diluted with water and 2M HCl. The resulting solid was collected by vacuum filtration and washed with cold water and 2M HCl. The product was recrystallized from xylene, dried under vacuum for 48 hours. 50mg of crystalline product was further purified by flash chromatography on a silica gel G column (100cm×2.5cm; 40 micron particle size) with a nitrogen pressure of 5–10 p.s.i. using ethyl acetate/xylene (2:1; v/v) as the running solvent. The eluant was tested using TLC (silica gel G plates) and THF/xylene (1:1; v/v) as the running solvent. The pure 4-coronenyl butyric acid (FIG. 1, compound III) exhibited a single spot (Rf=0.65) under these conditions. Fractions containing pure product were pooled and dried by rotary evaporation. A yield of 86% was obtained (66.4 mg) with a melting point of 273° C. IR and NMR analysis showed spectra consistent with the expected product. Compound III in THF had an absorption band $\epsilon_{294}$=23,644±97 80$M^{-1}cm^{-1}$.

Synthesis of 4-coronenyl butyric phosphatidylcholine (Cor-PC)

Redistilled triethylamine (9μl) was added to a stirred suspension of compound III (20mg) in dry methylene chloride (2ml), followed by 30 μl of trimethylacetyl chloride. The mixture was incubated at 25° C. to form the mixed anhydride. The reaction mixture was evaporated to dryness and held under 1 mm Hg vacuum for 60 minutes at 25° C. The residue was treated with 2 ml of methylene chloride, excess egg L-α-lysophosphatidylcholine (from Sigma Chemical Co., St. Louis, Mo.) and dimethylaminopyridine (9 mg). The solution was stirred for 12 hours at 25° C. The Cor-PC (FIG. 1, compound IV) was isolated from the reaction mixture by first diluting with chloroform and then extracted with three 10 ml portions of cold 0.01M HCl. The organic layer was dried by evaporation, redissolved in chloroform/methanol/acetic acid/water (75/25/7.5/2.5; v/v) and flash chromatographed using a silica gel G column (100 cm×2.5cm; 40 micron particle size) with a nitrogen pressure of 5–10 p.s.i. Fractions of 2ml were collected. TLC analyses using silica gel G and the same solvent system showed that unreacted compound III eluted first, followed by pure Cor-PC ($R_f$=0.36 using silica gel G and column running solvent). Fractions containing pure product were pooled and dried by rotary evaporation. Pure Cor-PC was stable for several months when dissolved in 95% ethanol and stored at −20° C. under nitrogen. The concentration of the fluorescent lipid analog (0.181 mM) was determined by phosphorus assay. Typical yields were 7% based on compound III. The material was homogenous by TLC examination exhibiting a single fluorescent spot which gave a positive spray reaction with phosphorous staining ammonium molybdate reagent. Incubation of pure Cor-PC (200μl of 0.181 mM solution taken to dryness under nitrogen and redissolved in 95% diethyl ether/methanol (95/5; v/v)) with phospholipase A$_2$ (1 mg in 1 ml of 0.22M NaCl-0.02M CaCl-0.001M EDTA-0.05M MOPS, pH 7.2) as described elsewhere (Biocherhoff, H. (1975) Methods in Enzymology 35, 318) yielded compound III and lysophosphatidylcholine, both identified by TLC. Pure Cor-PC in THF has an absorption band at 304 nm ($\epsilon_{304}$ nm=11,581M$^{-1}$cm$^{-1}$). MOPS (3-[N-Morpholino]propanesulfonic acid) and EDTA (Ethylenediaminetetraacetic acid) are commercially available reagents which are known in the art. The Biocherhoff procedure is also known in the art.

The following publications are hereby incorporated by reference:
1. Vincent et al., Biochemical and Biophysical Research Communications 107, 914 (1982).
2. Vincent et al., Biochemistry 21, 708 (1982).
3. Slepushkin et al., European Journal of Biochemistry 173, 599 (1988).
4. Molotkovsky et al., Chem. Phys. Lipids 58. 199 (1991).
5. Gromova et al., Chem. Phys. Lipids 60, 235 (1992)
6. Clar, E. and Zanders, M., J. Chem. Soc. 2, 1577-1579 (1958)
7. Morgan et al., Biochim et Biophys Acta, 692, 196 (1982).
8 J. R. Lakowicz; "Fluorescence Spectroscopy" Plenum Press, New York.
9 Biocherhoff, H. Methods in Enzymology 35, 318 (1975).

What is claimed is:

1. A fluorescent probe of formula I:

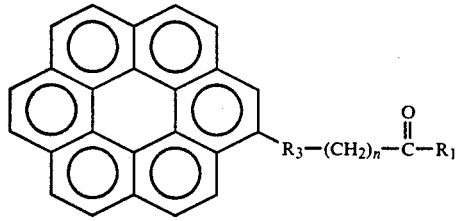

wherein:
R$_1$ is a lipid or membrane mimetic radical,
R$_3$ is methylene or carbonyl, and
n is 1 to 25.

2. The fluorescent probe of claim 1, wherein:
R$_1$ is a radical selected from sphingolipids, glycerolipids, diacylglycerols, ceramides, glycolipids, glycosphingolipids and cardiolipin.

3. The fluorescent probe of claim 1, wherein R$_1$ is a phospholipid radical.

4. The fluorescent probe of claim 3 wherein the phospholipid radical is a monoacylglycerol phosphate radical, a diacylglycerolphosphate radical, or a sphingomyelin radical.

5. The fluorescent probe of claim 1, wherein R$_1$ is hydroxyl.

6. The fluorescent probe of claim 1, wherein R$_1$ is a cholesterol radical.

7. A fluorescent probe of formula II:

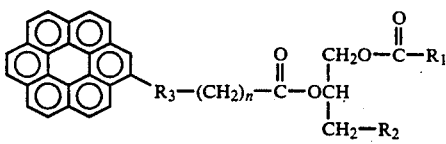

wherein:
n is 1 to 25,
R$_1$ is a straight chain hydrocarbon group of up to 25 carbon atoms in length, which may contain one or more double or triple bonds,
R$_2$ is phosphate, phosphocholine, phosphoinositol, phosphoserine, phosphoethanolamine, phosphoglycerol, substituted phosphoglycerol, or an oxygen bound to a carbonyl group bound to a straight chain hydrocarbon group of up to 25 carbon atoms in length, which may contain one or more double or triple bonds, and
R$_3$ is methylene or carbonyl.

8. A fluorescent probe of formula III:

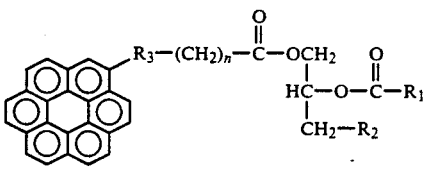

wherein,
n is 1 to 25,
R$_1$ is a straight chain hydrocarbon group of up to 25 carbon atoms in length, which may contain one or more double or triple bonds,
R$_2$ is phosphate, phosphocholine, phosphoinositol, phosphoserine, phosphoethanolamine, phosphoglycerol, substituted phosphoglycerol, or an oxygen bound to a carbonyl group bound to a straight chain hydrocarbon group of up to 25 carbon atoms in length, which may contain one or more double or triple bonds, and
R$_3$ is methylene or carbonyl.

9. A method of determining the lipid packing and lipid dynamics in a membrane comprising:
introducing the probe of claim 1 into a membrane by cosonication, coextrusion, or addition as a micelle;
measuring the rotational motion of the probe from steady state or time-resolved polarized fluorescence spectroscopy;
analyzing the polarized data to determine the emission anisotropy; and
thereby determining the lipid packing and lipid dynamics.

10. A method of estimating hydrodynamic properties of macromolecules or macromolecular complexes comprising:
chemically binding the probe of claim 5 to a macromolecule or macromolecular complex;
measuring the rotational motion of the probe from steady state or time-resolved polarized fluorescence spectroscopy;
analyzing the polarized data to determine the emission anisotropy; and thereby estimate hydrodynamic properties of the macromolecules or macromolecular complexes.

11. A method of measuring changes in a $Ca^{+2}$ concentration in or near a membrane comprising:

introducing the probe of claim 7 into a membrane by cosonication, coextrusion, or addition as a micelle;

introducing phospholipase $A_2$ into or near the membrane;

measuring the rotational motion of the released coronene probe using steady state or time-resolved polarized fluorescence spectroscopy;

analyzing the polarized data to determine the emission anisotropy; and thereby detecting changes in the $Ca^{+2}$ concentration.

* * * * *